United States Patent
Chang et al.

(10) Patent No.: US 10,653,348 B2
(45) Date of Patent: *May 19, 2020

(54) FOOT PULSE OXIMETER FOR SCREENING CONGENITAL HEART DISEASE BEFORE NEWBORN DISCHARGE

(71) Applicant: LOS ANGELES BIOMEDICAL RESEARCH INSTITUTE AT HARBOR-UCLA MEDICAL CENTER, Torrance, CA (US)

(72) Inventors: Ruey-Kang Chang, Diamond Bar, CA (US); Yann Ping Pan, Diamond Bar, CA (US)

(73) Assignee: LOS ANGELES BIOMEDICAL RESEARCH INSTITUTE AT HARBOR-UCLA MEDICAL CENTER, Torrance, CA (US)

( * ) Notice: Subject to any disclaimer, the term of this patent is extended or adjusted under 35 U.S.C. 154(b) by 224 days.

This patent is subject to a terminal disclaimer.

(21) Appl. No.: 15/682,412

(22) Filed: Aug. 21, 2017

(65) Prior Publication Data

US 2017/0347931 A1 Dec. 7, 2017

Related U.S. Application Data

(63) Continuation of application No. 13/216,150, filed on Aug. 23, 2011, now Pat. No. 9,763,606.
(Continued)

(51) Int. Cl.
*A61B 5/1455* (2006.01)
*A61B 5/024* (2006.01)
*A61B 5/00* (2006.01)

(52) U.S. Cl.
CPC ...... *A61B 5/14552* (2013.01); *A61B 5/02438* (2013.01); *A61B 5/6829* (2013.01)

(58) Field of Classification Search
CPC ... A61B 5/0205; A61B 5/024; A61B 5/02438; A61B 5/1455; A61B 5/14551;
(Continued)

(56) References Cited

U.S. PATENT DOCUMENTS

| 5,125,403 A | 6/1992 | Culp |
| 5,842,982 A | 12/1998 | Mannheimer |

(Continued)

FOREIGN PATENT DOCUMENTS

| CN | 1657007 | 8/2005 |
| WO | 2005065540 | 7/2005 |

OTHER PUBLICATIONS

Chang RK, Gurvitz M, Rodriguez S. Missed diagnosis of critical congenital heart disease. Arch Pediatr Adolesc Med. Oct. 2008;162(10):969-974.
(Continued)

*Primary Examiner* — Eric F Winakur
*Assistant Examiner* — Chu Chuan Liu
(74) *Attorney, Agent, or Firm* — Pillsbury Winthrop Shaw Pittman LLP

(57) ABSTRACT

A method including placing a portion of a foot of a newborn in a device, the device including a light emitter and a corresponding receiver coupled on opposite sides of the device, the device further including a processor for processing data from the light emitter and receiver; and determining a presence of congenital heart disease. An apparatus including a body including a chamber of a size to accommodate a portion of a newborn's foot; at least one light emitter and a corresponding detector coupled on opposite sides of the body, the emitter configured to emit light of a prescribed wavelength into the chamber; and a processor coupled to the body and configured to receive a signal from the at least one detector.

20 Claims, 9 Drawing Sheets

Related U.S. Application Data

(60) Provisional application No. 61/375,875, filed on Aug. 23, 2010.

(58) Field of Classification Search
CPC ............ A61B 5/14552; A61B 5/14532; A61B 5/6829; A61B 5/72; A61B 5/7203
See application file for complete search history.

(56) References Cited

U.S. PATENT DOCUMENTS

| | | | |
|---|---|---|---|
| 5,978,691 A * | 11/1999 | Mills ................... | A61B 5/14552 600/326 |
| 6,047,201 A | 4/2000 | Jackson, III | |
| 6,470,199 B1 | 10/2002 | Kopotic et al. | |
| 6,510,331 B1 | 1/2003 | Williams | |
| 6,553,243 B2 * | 4/2003 | Gurley ................... | A61B 42/20 600/340 |
| 6,615,065 B1 | 9/2003 | Barrett | |
| 7,171,251 B2 | 1/2007 | Sarussi et al. | |
| 7,190,987 B2 | 3/2007 | Lindekugel et al. | |
| 2002/0028990 A1 | 3/2002 | Shepherd et al. | |
| 2002/0133067 A1 | 9/2002 | Jackson, III | |
| 2004/0116787 A1 | 6/2004 | Schnall | |
| 2004/0260161 A1 | 12/2004 | Melker et al. | |
| 2005/0197551 A1 | 9/2005 | Al-Ali et al. | |
| 2006/0069319 A1 | 3/2006 | Elhag | |
| 2006/0189871 A1 | 8/2006 | Al-Ali | |
| 2007/0088341 A1 | 4/2007 | Skiba et al. | |
| 2008/0009754 A1 * | 1/2008 | Chang ................... | A61B 5/0205 600/483 |
| 2008/0071155 A1 | 3/2008 | Kiani | |
| 2011/0015498 A1 | 1/2011 | Mestrovic et al. | |
| 2012/0046532 A1 | 2/2012 | Chang | |
| 2012/0253153 A1 | 10/2012 | Trumble | |

OTHER PUBLICATIONS

Hoffman JI. It Is Time for Routine Neonatal Screening by Pulse Oximetry. Neonatology. Jun. 4;99(1):1-9.

Chang RK, Rodriguez S, Klitzner TS. Screening newborns for congenital heart disease with pulse oximetry: survey of pediatric cardiologists. Pediatr Cardiol. Jan. 2009;30(1):20-25.

Mahle WT, Newburger JW, Matherne GP, et al. Role of pulse oximetry in examining newborns for congenital heart disease: a scientific statement from the American Heart Association and American Academy of Pediatrics. Circulation. Aug. 4, 2009;120(5):447-458.

Notice of Allowance dated Oct. 12, 2017 issued in corresponding U.S. Appl. No. 14/515,820.

\* cited by examiner

FOOT PULSE OXIMETER FOR SCREENING CONGENITAL HEART DISEASE BEFORE NEWBORN DISCHARGE

CROSS-REFERENCE TO RELATED APPLICATIONS

This application is a continuation of U.S. patent application Ser. No. 13/216,150 filed on Aug. 23, 2011 and entitled "FOOT PULSE OXIMETER FOR SCREENING CONGENITAL HEART DISEASE BEFORE NEWBORN DISCHARGE," which claims the benefit of the earlier filing date of U.S. Provisional Patent Application No. 61/375,875, filed Aug. 23, 2010, both of which are incorporated herein by reference in their entireties.

FIELD

Pulse oximetry and congenital heart disease.

BACKGROUND

Pulse oximetry is used to measure the arterial oxygen saturation of hemoglobin ($SpO_2$) and pulse rate of a patient. Measurement of these characteristics is accomplished by use of a non-invasive sensor which scatters red and infrared lights through a portion of the patient's tissue where arterial blood perfuses the tissue. The sensor then senses the absorption of light photoelectrically by the tissue. The differential amounts of red and infrared light absorbed are then used to calculate the percentage of hemoglobin in the arterial blood that is saturated with oxygen.

Pulse oximetry is commonly used as a monitoring device in the emergency departments, intensive care units, observational units, and operating rooms. Most pulse oximeter probes are designed for prolonged, continuous monitoring of the $SpO_2$ and pulse rate of a patient. These probes are generally shaped as a clip for the finger or toe, or for infant using adhesive tapes for wrapping around the foot. For spot check of $SpO_2$ or for the purpose of screening, using disposable probes is time consuming and not cost effective.

Congenital heart disease (CHD) affects 8 per 1,000 liveborn infants and is one of the most common and serious types of birth defect. If diagnosed early, CHD can be managed with successful surgical repair or palliation for the majority of infants. A missed or delayed diagnosis can be life threatening or result in long-term morbidities for these infants. Current clinical practice for detecting CHD in newborns relies on a clinician performing a physical examination before the child's routine discharge from the nursery. A significant number of newborns with CHD are missed by routine physical examination.

In recent years, health care professionals have found pulse oximetry an important screening tool to aid clinical examination for detecting some severe forms of CHD. In a 2007 survey of 1,086 pediatric cardiologists, the majority of respondents support a mandate for universal screening by pulse oximetry before newborn discharge. In 2009, the American Heart Association and American Academy of Pediatrics jointly issued a scientific statement recommending routine pulse oximetry screening on the foot of asymptomatic newborns after 24 hours of life, but before hospital discharge.

The commonly used pulse oximetry sensors require attachment to the fingers or toes. In infants and neonates, the fingers and toes are too small for the clip-type of pulse oximetry sensor commonly used in older children and adults. Commonly used approaches include taping the pulse oximetry sensor in place on the finger/toe or hand/foot by adhesives or by Velcro. These sensors are generally single-use therefore adds substantial expenses to the universal screening of all newborn at hospital discharge. Taping a pulse oximetry sensor on an infant's toe or foot takes a considerable amount of time, which adds difficulty to screen a large number of newborns. Furthermore, the taping the pulse oximetry sensors on the toe or the foot is prone to motion artifacts, and signal interferences from ambient lights, which are less than ideal to be used in a setting of newborn screening. To summarize, the current pulse oximetry sensors cannot be used for newborn CHD screening because the single-use sensors add to the cost, takes a significant amount of time to place the sensors, and are prone to artifacts from motion and ambient light.

Kiani (US 2008/0071155 A1) teaches an invention of a congenital heart disease monitor using a pulse oximeter. The pulse oximeter uses conventional finger or wrap around probes to measure $SpO_2$ from upper and lower extremities.

Mannheimer (U.S. Pat. No. 5,842,982) teaches an improved infant/neonatal pulse oximeter sensor that attaches to an infant's foot. A pad conforms to the heel of an infant, with the light emitter and a detector being mounted below the achilles tendon and below the calcaneus bone. The heel pad can be held in place with a stretchable sock.

Jackson III (US 2002/0133067 A1) discloses an invention of a SIDS warning device by a pulse oximeter mounted in a woven foot wrap. This device uses a low-powered transmitter to transmit readings to a remote monitoring unit. The wrapping is made of an opaque elastic material that secure not only around the arch and ball area of the infant's foot, but also around the ankle. The pulse oximeter will be placed in the wrap on the dorsal and plantar area near the arch of the infant's foot.

Pulse oximter probes to be used at other parts of the body have been proposed by other inventors. Melker et al (US 2004/0260161 A1) teaches a pulse oximeter probe to be used on the lip or cheek. Melker et al (WO 2005/065540 A1) also teaches a pulse oximeter probe to be used on the nose. Shepard et al (US 2002/0028990 A1) teaches a pulse oximeter probe to be used in the posterior pharynx. Although these pulse oximeter probes may be useful for patient monitoring, they cannot be used on newborns. Furthermore, the American Academy of Pediatrics specifically recommends the pulse oximetry to be performed on the foot for the purpose of screening for critical congenital heart disease.

BRIEF DESCRIPTION OF THE DRAWINGS

FIG. 1 is an illustration of one embodiment of a newborn pulse oximeter device with a hollow space in the center to place a newborn's foot in.

DESCRIPTION OF THE PREFERRED EMBODIMENT

Figure 1:
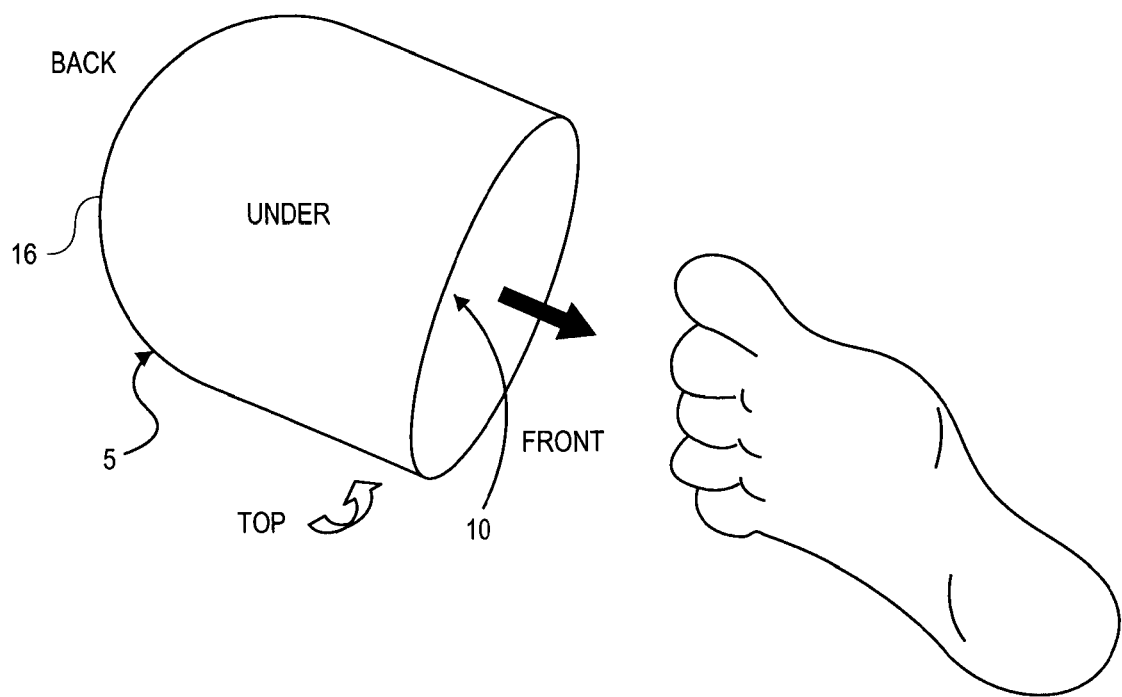

FIG. 1 illustrates one embodiment of a newborn pulse oximeter device. In this embodiment, device 5 has a tubular body with an open front end. The tubular body defines hollow space or chamber 10 sized to accommodate at least a portion of a newborn's foot (toes first) for signal acquisition. Opposite the open front end of case 16 of device 5, in this embodiment, the case has a closed back end. As illustrated, in one embodiment, the closed back end has a dome shape. It is appreciated that other shapes are possible (e.g., flat, pyramidal, etc.). In another embodiment, the closed back end may be open or partially open. It is further appreciated that, although case 16 of device 5 is shown having a tubular shape, other shapes are possible, so long as a portion of a newborn's foot can fit inside. Details of device 5 are further illustrated in FIGS. 2, 3 and 6.

Figure 2:
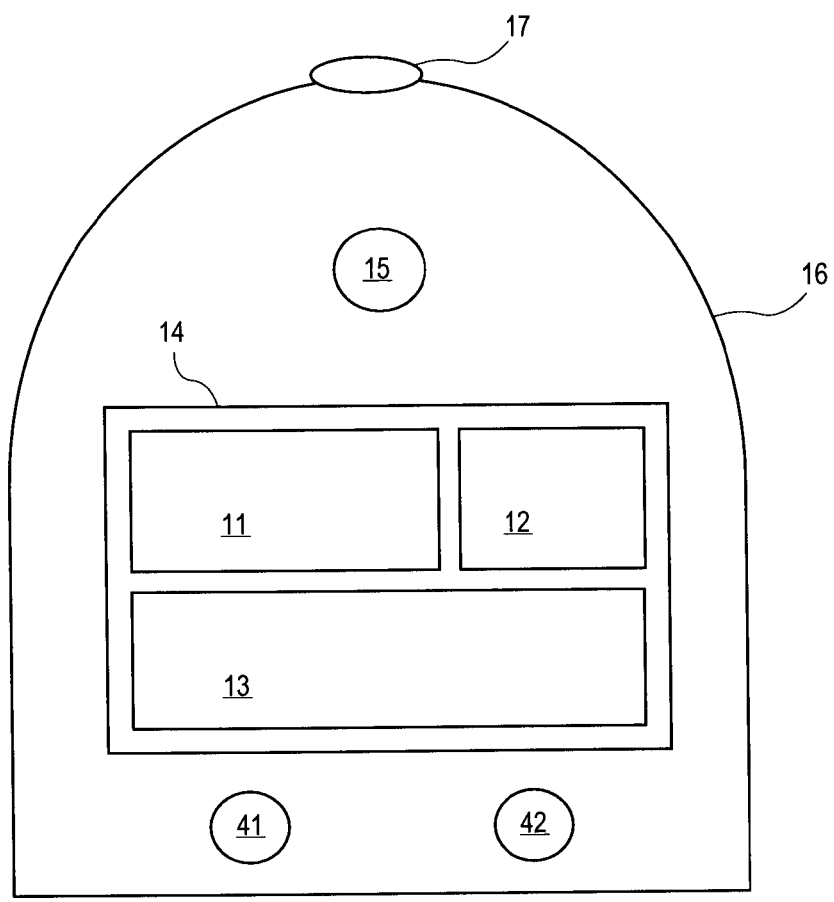
FIG. 2 is a diagram showing a top surface of the newborn pulse oximeter device shown in FIG. 1.

FIG. 2 shows a top side surface of device 5. In one embodiment, case 16 of device 5 is made of a cellulose-based plastic. A top surface of case 16 contains components to control an operation of the device and provide information. Two main components of the top surface are power button 15 and display 14. In display 14, signals representative of one or more of $SpO_2$ (oxygen saturation), heart rate, and arterial pulse waveforms may be displayed. Referring to display 14 of FIG. 2, the signals are displayed in panel 11 as $SpO_2$, panel 12 as heart rate, and panel 13 as arterial pulse waveforms. Display 14 is, for example, a liquid crystal display (LCD). In one embodiment, there are two indicator lights (41 and 42). Indicator light 41 displays the quality and strength of the pulse signals, using, for example, a green color indicator for good signal quality, an amber color as questionable or borderline signal quality, and a red color as poor signal quality. Indicator 42 provides a pass/fail indication for a congenital heart disease. When, for example, a newborn's foot is placed in device 5 and there are greater than 10 seconds of a green color signal on indicator 41, and the $SpO_2$ reading on panel 11 is equal or greater than 95 percent, indicator 42 will display a green color light to indicate that the newborn has passed the screening test. When there are greater than 10 seconds of a green color signal on indicator 41, and the $SpO_2$ reading on panel 11 is lower than 95 percent, indicator 42 will display a red color light to indicate that the newborn has failed the screening test. In one embodiment, port 17 in the back side of the oximeter is used for connecting to an external pulse oximeter probe which can be the conventional finger clip on probe or existing infant probes with adhesive tapes for wrapping around the foot.

Figure 3:
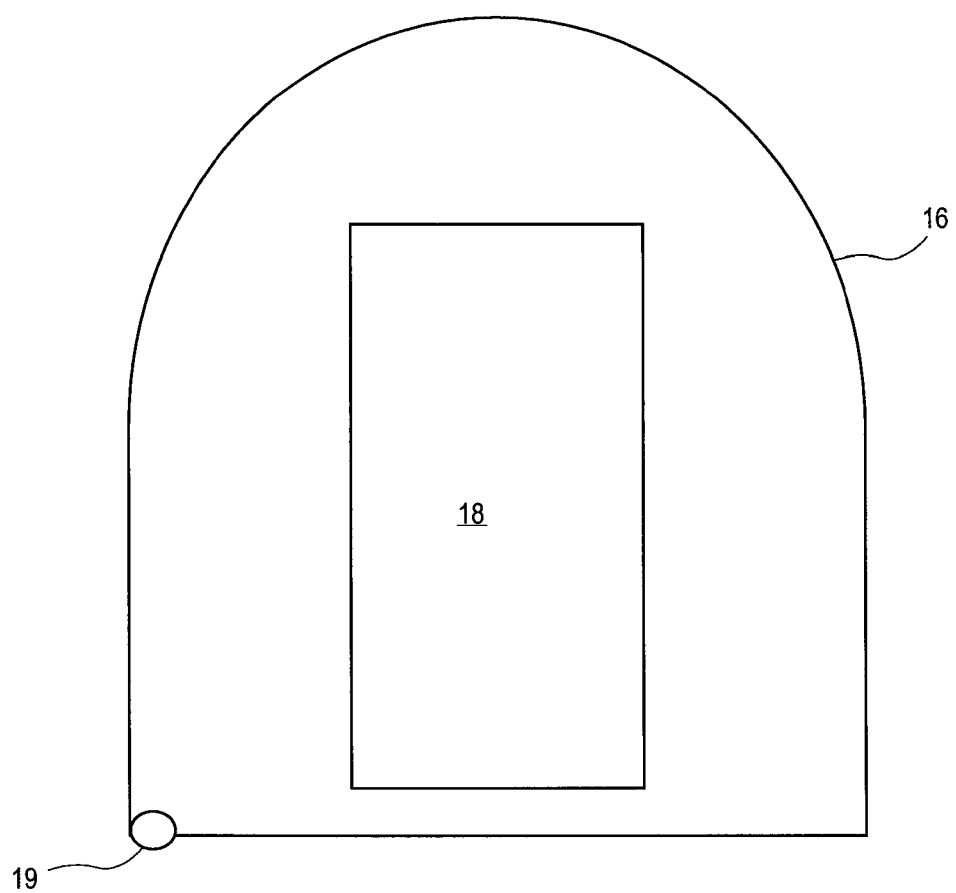
FIG. 3 is a diagram showing an under surface of the newborn pulse oximeter device shown in FIG. 1.

FIG. 3 shows an under side surface of newborn pulse oximeter device 5. In one embodiment, device 5 is battery-operated. Accordingly, an under side surface of device 5 includes a battery compartment 18 with a removable cover. In one embodiment, the batteries are standard AAA or AA batteries that can be replaceable when needed. In another embodiment, the batteries are lithium based rechargeable batteries. An under side surface of device 5 also includes, in this embodiment, connector 19 that is used for plugging device 5 to an AC adaptor for battery charging or as a separate power source for device 5.

Figure 4:
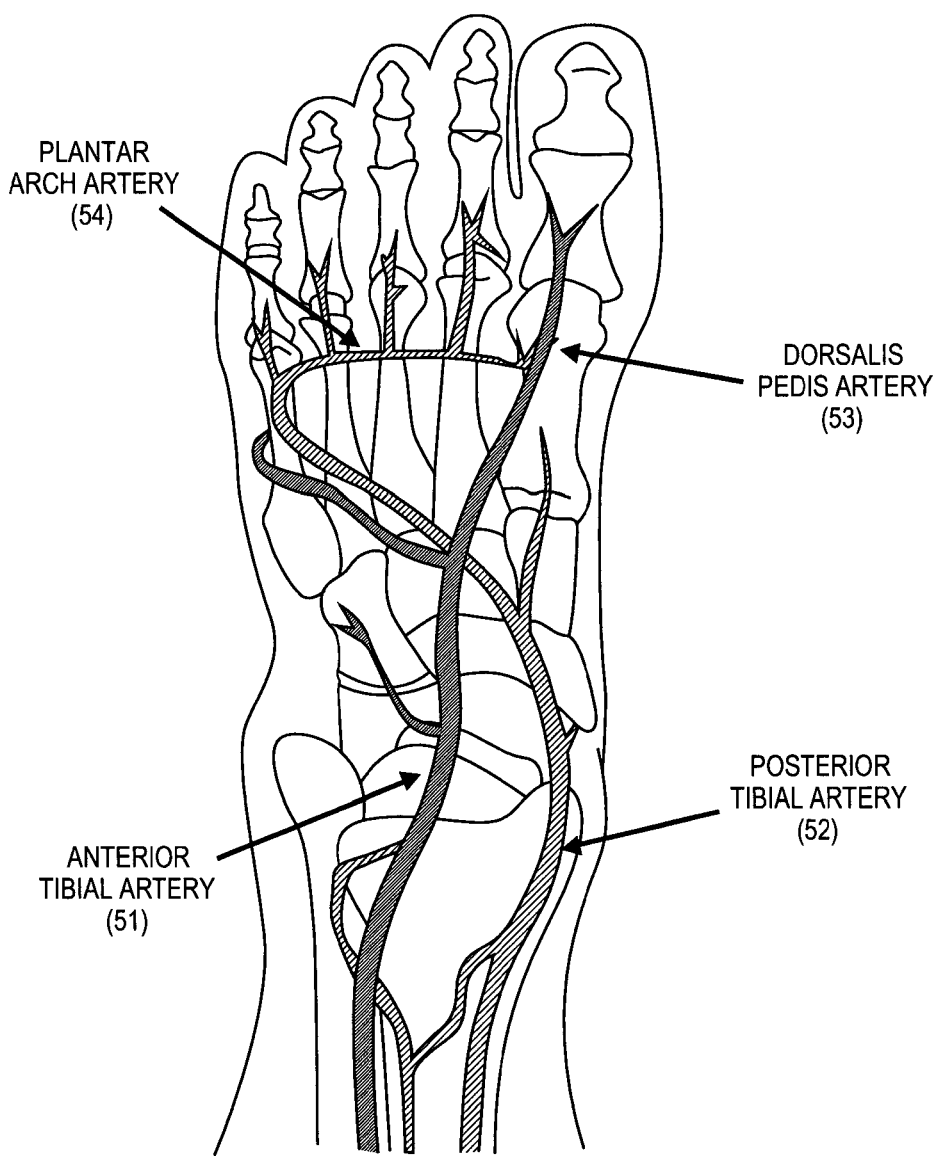
FIG. 4 is an illustration of the arterial blood supply of the foot.

FIG. 4 is an anatomical illustration of the arterial blood supply of the foot. The two major arteries to the foot are anterior tibial artery 51 and posterior tibial artery 52. Anterior tibial artery 51 branches to dorsalis pedis artery 53 which courses through the dorsal side of the foot to the first toe. Posterior tibial artery 52 courses through the ventral side of the foot and becomes plantar arch artery 54.

Figure 5:
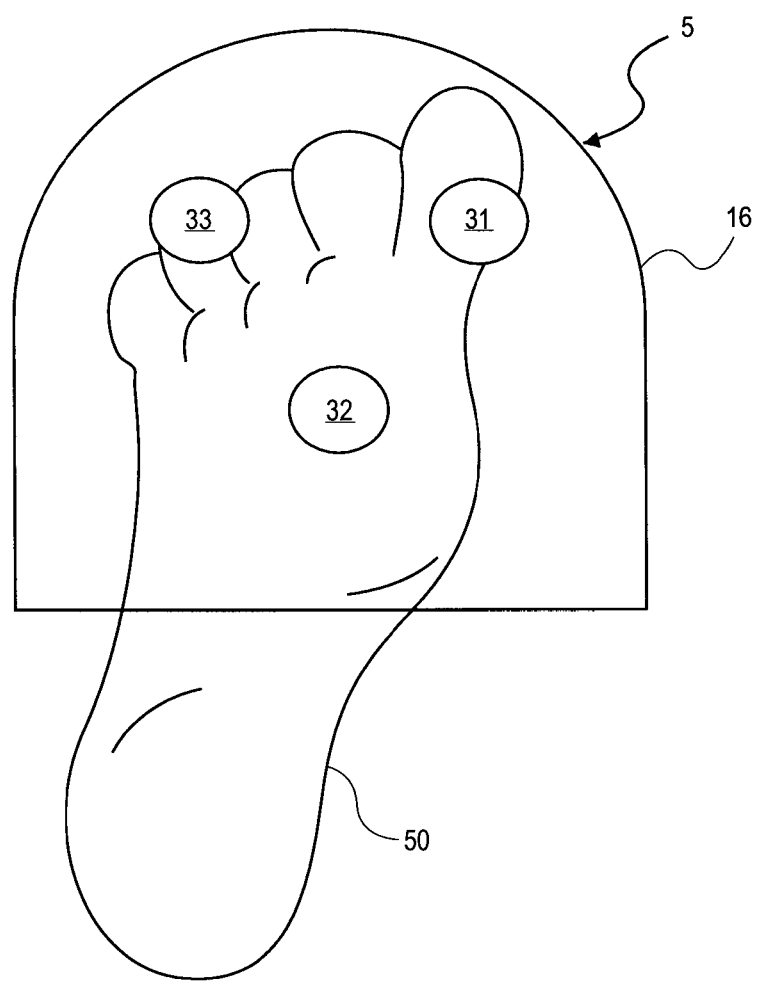
FIG. 5 is an illustration of the positions of emitters and receivers inside the newborn pulse oximeter device of FIG. 1 for detecting signals from the arteries of the newborn's foot.

FIG. 5 is an illustration of the positions of light emitters and receptors associated with device 5. In one embodiment, the light emitters and detectors are connected to device 5, such as connected (adhered) to case 16 in chamber 10 to emit light and receive light in chamber 10. In one embodiment, there are three pairs of light emitters 21, 22, 23 and receivers (31, 32, 33) of device 5. It is appreciated that there can be more or less than three pairs of light emitters and detectors. The illustration is a view from an under side surface of device 5 and the ventral surface of foot 50, therefore, receivers 31, 32, 33 are shown, but emitters 21, 22, 23 are, on the other side of foot 50, are not shown in the illustration of FIG. 5. The pair of emitter/receiver 21/31 are separately connected to case 16 and positioned inside chamber 10 to detect the pulse signals from dorsalis pedis artery 53 of the first toe when the infant's right foot is placed inside the chamber 10 of device 5. The pair of emitter/receiver 23/33 are separately connected to case 16 and positioned inside chamber 10 to detect the pulse signals from dorsalis pedis artery 53 of the first toe when the infant's left foot is placed inside the chamber 10. The pair of emitter/receiver 22/32 are separately connected to case 16 and positioned inside chamber 10 to detect the pulse signals from plantar arch artery 54 of the foot when either the right foot or left foot is placed inside chamber 10. In one embodiment, each emitter emits a light at red (660 nanometers (nm)) and a light at infrared (940 nm), possibly modulated, to pass through a newborn's foot and be detected by the corresponding detector. Each emitter 21, 22, 23 is electrically connected to a processor and instruction logic in the processor directs the emission of light (red and infrared) from each emitter. Likewise, each receiver 31, 32, 33 is electrically connected to the processor and transmits received signals to the processor. A receiver produces an electrical signal corresponding to the red and infrared light energy attenuated from transmission through a newborn's foot.

Pulse oximetry uses the differential light absorption of oxygenated hemoglobin $HbO_2$, and deoxygenated hemoglobin, Hb, to compute their relative concentrations in the arterial blood. The arterial saturation of hemoglobin, $SpO_2$, may then be calculated as $SpO_2 = 100 \, C_{HbO2}/(C_{Hb}+C_{HbO2})$.

Figure 6:
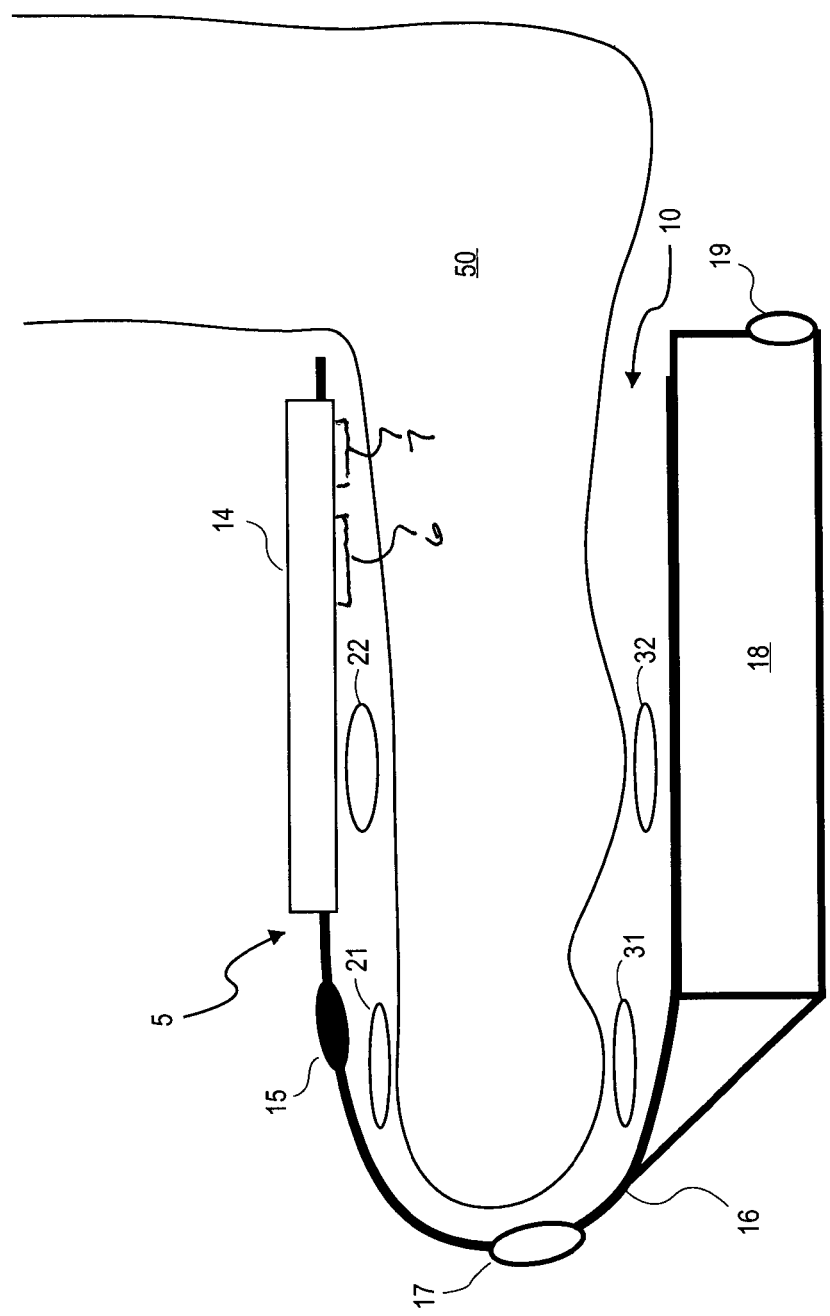
FIG. 6 is an illustration of the longitudinal section view of the newborn pulse oximeter device of FIG. 1 with the newborn's foot in the oximeter.

FIG. 6 is an illustration of a longitudinal sectional view of pulse oximeter device 5 with a newborn's foot in chamber 10. In this view, light emitters 21, 22, 23 are located on the top side of the chamber, and the paired receivers 31, 32, 33 located on the bottom side directly opposite the paired emitters. When the newborn's foot 50 is inside chamber 10, the paired emitter and receiver are on either side of foot 50 in order to have the infrared and red lights traverse through dorsalis pedis artery 53 or plantar arch artery 54. Power button 15 and LCD display 14 are on the top surface of the oximeter as viewed. FIG. 6 also shows processor 6 and memory 7 in or on case 16 on a top side of device 5 as viewed. Processor 6 is electrically connected to emitters 21, 22, 23; to receivers 31, 32, 33; and to port 17. Battery compartment 18 and charging port 19 are located on the under side of the oximeter.

Figure 7:
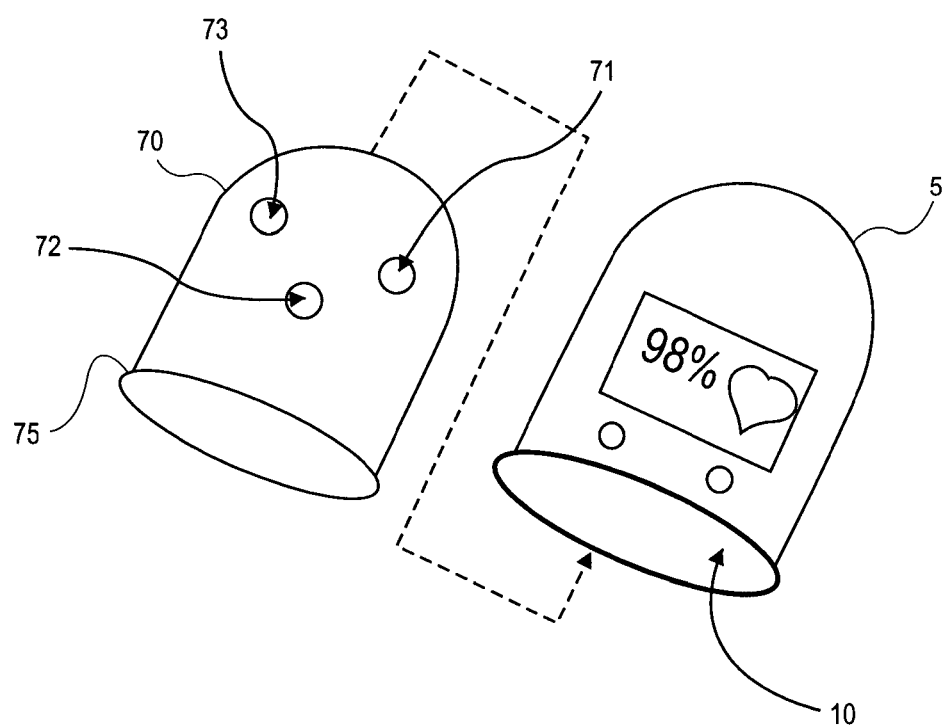
FIG. 7 is a top side view illustration of a cover that may be positioned within the newborn pulse oximeter device of FIG. 1.

In one embodiment, a single use interior cover for pulse oximeter device 5 will be used to protect a newborn's skin, prevent infection and enhance signal acquisition. FIG. 7 shows disposable cover 70 shaped to fit within the interior of device 5 (in chamber 10) before placing a newborn's foot into chamber 10. Representatively, cover 70 is made of a thin polyurethane membrane and shaped to fit the interior of the device. The membrane may be translucent or is translucent in the six locations (shown are three locations 71, 72, 73) that correspond to the locations of the three pairs of light emitters 21, 22, 23 and their respective receivers 31, 32, 33 in the device. By using a design where only the six locations of the membrane are translucent, there is a reduction in potential "noise" and the chance of optical detector saturation from ambient lights. It will also minimize light scattering from the interior of the unit from emitters in one channel to the receiver of another channel. As shown in FIG. 7, in one embodiment, cover 70 includes plastic ring 75 at the end opening of cover 70 to provide a shape of the cover similar to a shape of chamber 10 of device 5. An applicator may be used for easy placement of cover 70 into device 5. A membrane of cover 70 may be impermeable to microorganisms and pre-sterilized to protect against infection. No adhesives need to be applied to the side of the membrane with skin contact to avoid irritation. Polyurethane is commonly used in surgical implants and is the material in Tegaderm® (3M), which has been used extensively in neonates with very low rate of skin irritation or allergy.

Figure 8:
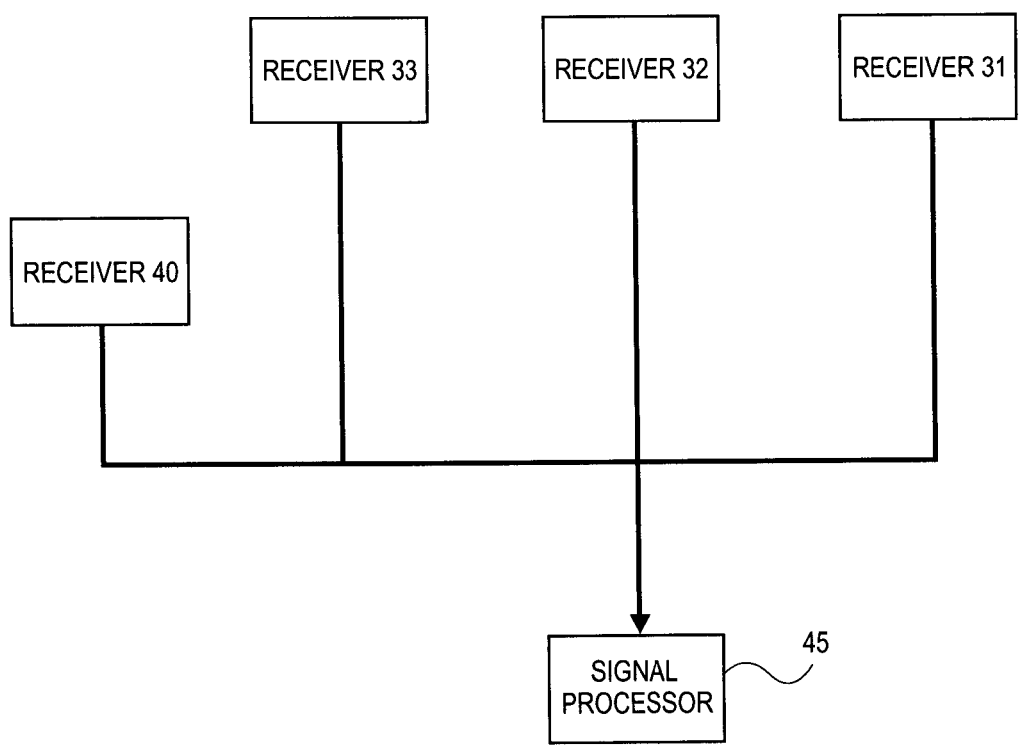
FIG. 8 is a diagram showing the electrical connections of the receivers to the signal processor for the newborn pulse oximeter device of FIG. 1.

FIG. 8 is a diagram showing the electrical and signal connections of the receivers 31, 32, 33 to signal processor 45 of pulse oximeter device 5. Receiver 40 is an optional external oximeter probe connected to the oximeter via port 17 (see FIG. 2). Signal processor 45 receives signals from receivers 31, 32, 33 and 40 and processes the signals based on the algorithm stored in a memory associated with signal processor 45 in device 5. In one embodiment, signal processor contains program instructions in machine readable form to receive from receiver(s) emitted signals from the emitter(s) directly connected to the device (emitters 21, 22, 23) or from an external receiver (e.g., receiver 40) and determine the best quality signal(s). Signal processor 45 also contains instructions to perform a machine readable method to determine $SpO_2$ and pulse rate based on received signals from receivers directly connected to the device (31, 32, 33) or external to it and to make a determination of congenital heart disease if, for example, an $SpO_2$ reading is below 95 percent for a period of time. Signal processor 45 performs its program instructions (e.g., a machine readable method) and displays data and results at display 14 and indicator lights 41 and 42.

Figure 9:
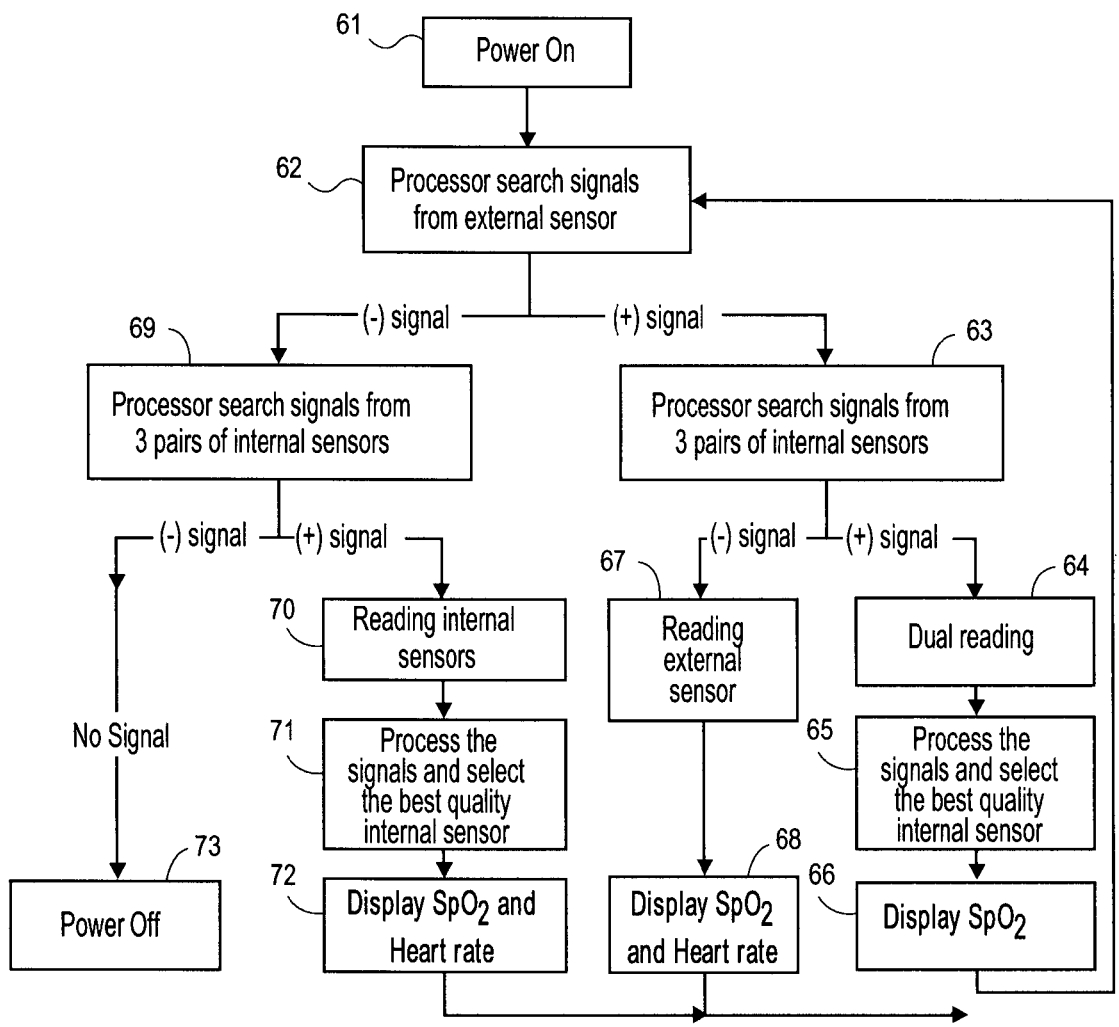
FIG. 9 is a diagram showing the algorithm for signal processing and power management for the newborn pulse oximeter device of FIG. 1.

FIG. 9 shows algorithm 60 for signal processing and power management of pulse oximeter device 5. When an operator pushes power button 15 to turn device 5 on (block 61), signal processor 45 will first search signals from external receivers (e.g., receiver 40, FIG. 8) (block 62). If signal(s) are found from external receiver(s), signal processor 45 will search signals from internal receivers 31, 32, 33 (block 63). If signal(s) are found, signal processor 45 can interpret both internal (e.g., lower extremity (foot)) and external (e.g., upper extremity) signals (block 64). Processor 45 will then identify the best quality internal signals (block 65), and display the results of the internal and external signals on display 14 (see FIG. 2) (block 66). The quality of the signals will be shown by indicator light 41 (see FIG. 2).

If no signals are found in receivers 31, 32 or 33, processor 45 will read only the signal(s) from external receiver(s) and display signals from the external receiver(s) (blocks 67 and 68).

If no signals from external receiver(s) are found initially (block 62), processor 45 will search for signals from internal receivers 31, 32, 33 (block 69). If signals are found from internal receivers 31, 32, 33, processor 45 will read such signals (block 70) and select the best quality signal (block 71). The best quality signal (from receivers 31, 32, 33) will be processed and displayed on display 14 (block 72). If no signals from internal receivers 31, 32, 33 are found, the power will be turned off (block 73).

As will be understood by those skilled in the art, the current invention may be embodied in other forms without departing from the essential characteristics thereof. The foregoing description is intended to be illustrative, but not limiting, of the scope of the invention which is set forth in the following claims.

The invention claimed is:

1. A method comprising:
    placing a portion of a foot of a newborn in a device, the device comprising;
        a light emitter and a corresponding receiver coupled on opposite sides of the device,
        a processor for processing data from the light emitter and receiver;
        a chamber configured to receive the portion of the foot of the newborn, and
        a cover configured to be inserted into the chamber and form a double layer structure with the chamber, the cover configured to cover the portion of the foot of the newborn when the portion of the foot of the newborn is in the chamber,
            wherein placing the portion of the newborn's foot in the device comprises placing the cover into the chamber, and placing the portion of the newborn's foot into the cover, such that the cover covers the portion of the newborn's foot within the chamber, and
            wherein the cover comprises translucent areas and non-translucent areas, locations of the translucent areas positioned to correspond to positions of the light emitter and the receiver, and
    determining a presence of congenital heart disease in the newborn based on the data from the light emitter and receiver.

2. The method of claim 1, wherein the device comprises three or more light emitter/receiver pairs, and the cover comprises additional corresponding translucent areas positioned to correspond to the light emitters and receivers in the three or more light emitter/receiver pairs, the method further comprising detecting one or more best quality signals from the three or more light emitter/receiver pairs for the newborn's foot for display and analysis.

3. The method of claim 2, wherein the light emitter/receiver pairs are positioned on the device to detect signals from a *dorsalis* pedis artery at a first toe of the foot of the newborn or from a plantar arch artery.

4. The method of claim 2, wherein the device further comprises a power button and a display on the device.

5. The method of claim 4, wherein the display displays $SpO_2$, heart rate and arterial pulse waveforms in response to the data from the light emitter and the receiver.

6. The method of claim 1, wherein the processor comprises an algorithm configured to determine a signal quality of a signal from the receiver, to process the data from the light emitter and receiver in the signal, and display SpO$_2$, heart rate and waveform results on a display of the device.

7. The method of claim 1, further comprising indicating on the device the determination of the presence of congenital heart disease.

8. The method of claim 7, wherein determining the presence of congenital heart disease comprises determining an arterial saturation of hemoglobin (SpO$_2$).

9. The method of claim 8, further comprising indicating the presence of congenital heart disease when the SpO$_2$ is equal to or lower than a predetermined threshold.

10. The method of claim 9, wherein the SpO$_2$ predetermined threshold is 94 percent.

11. The method of claim 8, wherein the SpO$_2$ predetermined threshold can be configured by a user.

12. The method of claim 2, wherein the one or more best quality signals are selected from among a larger number of signals from external and/or internal receivers.

13. An apparatus comprising:
a body comprising a chamber of a size to accommodate a portion of a newborn's foot;
a cover configured to be inserted into the chamber and form a double layer structure with the chamber, the cover configured to cover the portion of the newborn's foot when the portion of the newborn's foot is in the chamber;
at least one light emitter and a corresponding detector coupled on opposite sides of the body, the emitter configured to emit light of a prescribed wavelength into the chamber; wherein the cover comprises translucent areas and non-translucent areas, locations of the translucent areas positioned to correspond to positions of the light emitter and detector, and
and
a processor coupled to the body and configured to receive a signal from the detector, and determine a presence of congenital heart disease in the newborn based on data in the signal from the detector.

14. The apparatus of claim 13, further comprising three or more light emitter/detector pairs, wherein the cover comprises additional corresponding translucent areas positioned to correspond to the light emitters and detectors in the three or more light emitter/detector pairs, and wherein the processor is configured to detect one or more best quality signals from the emitter/detector pairs for the newborn's foot for display and analysis.

15. The apparatus of claim 14, wherein the light emitter/detector pairs are positioned on the body to detect signals from a *dorsalis* pedis artery at a first toe of the foot or from a plantar arch artery.

16. The apparatus of claim 13, further comprising a display coupled to the body.

17. The apparatus of claim 16, wherein the display displays SpO$_2$, heart rate and arterial pulse waveforms in response to data produced by the light emitter and the detector.

18. The apparatus of claim 16, wherein the processor comprises an algorithm configured to determine a signal quality of a signal from the detector, to process data from the light emitter and the detector in the signal, and display at least one of SpO$_2$, heart rate and a waveform result on the display.

19. The apparatus of claim 17, further comprising at least one indicator light on the body, wherein the processor is configured to cause the indicator to indicate a presence of congenital heart disease based on data the processor processes from the at least one emitter and corresponding detector.

20. The system of claim 14, wherein the one or more best quality signals are selected from among a larger number of signals from external and/or internal detectors.

* * * * *